United States Patent [19]
Enevoldson

[11] Patent Number: 4,896,917
[45] Date of Patent: Jan. 30, 1990

[54] CHAIR FOR X-RAY TABLE

[75] Inventor: Eldon D. Enevoldson, Dayton, Ohio

[73] Assignee: Rehab Tech., Inc., Dayton, Ohio

[21] Appl. No.: 254,884

[22] Filed: Oct. 7, 1988

[51] Int. Cl.$^4$ .......................... A47C 3/18; A61G 7/10
[52] U.S. Cl. ..................... 297/217; 5/81 R;
297/349; 297/DIG. 4
[58] Field of Search ......... 297/192, 217, 252, DIG. 4;
5/61, 62, 81 R; 269/323

[56] References Cited

U.S. PATENT DOCUMENTS

| | | | |
|---|---|---|---|
| 2,836,223 | 5/1958 | Kent | 297/252 |
| 3,640,520 | 2/1972 | Wieland et al. | 5/63 X |
| 3,990,745 | 11/1976 | Rodaway | 297/444 |
| 4,016,005 | 4/1977 | DiMatteo | 297/DIG. 4 X |
| 4,240,169 | 12/1980 | Roos | 297/DIG. 4 X |
| 4,498,704 | 2/1985 | Hildreth | 297/397 |
| 4,699,425 | 10/1987 | Ohlson | 297/DIG. 4 X |
| 4,726,082 | 2/1988 | DiMatteo | 5/81 R |
| 4,770,467 | 9/1988 | Zinn | 297/DIG. 4 X |

FOREIGN PATENT DOCUMENTS 667013 2/1952 United Kingdom ............... 297/414

*Primary Examiner*—Peter R. Brown
*Attorney, Agent, or Firm*—Wood, Herron & Evans

[57] ABSTRACT

A chair for an X-ray table has a base that can be fixed to a foot plate projecting from the X-ray table. A seat is mounted on the base by means of a mechanism having a swivel, a fore and aft slide and a left and right slide. When the X-ray table is in a vertical attitude with the chair mounted on the foot plate, the seat can be pulled away from the table, turned left or right and returned to the table to hold the patient in the desired positions for fluoroscopic examination.

4 Claims, 2 Drawing Sheets

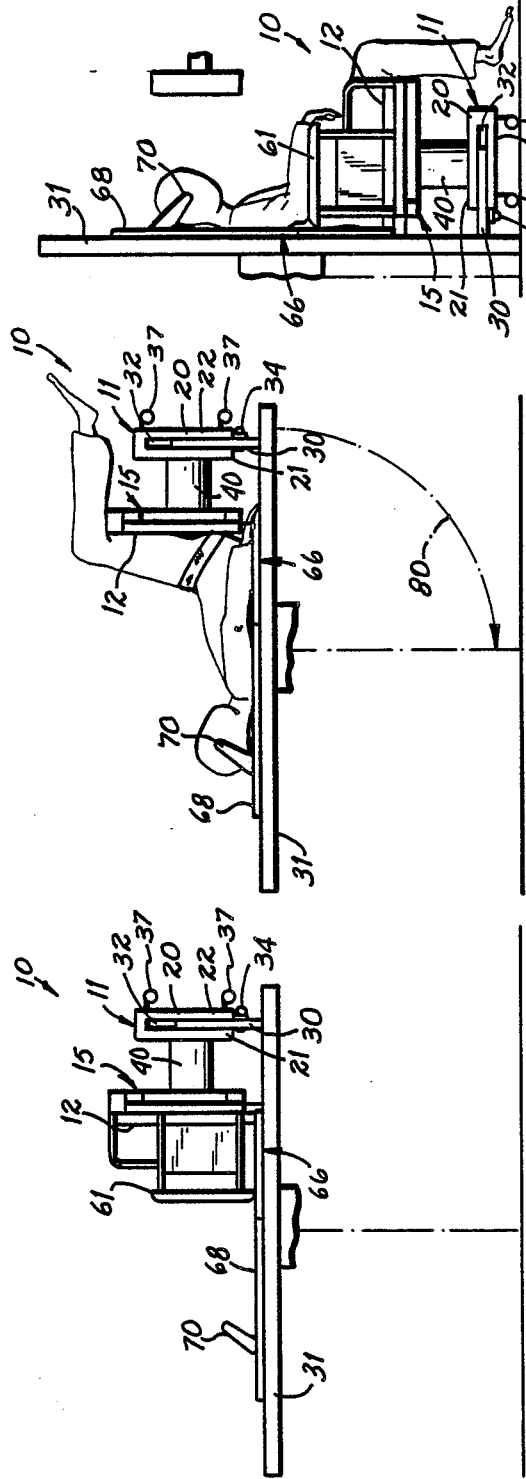
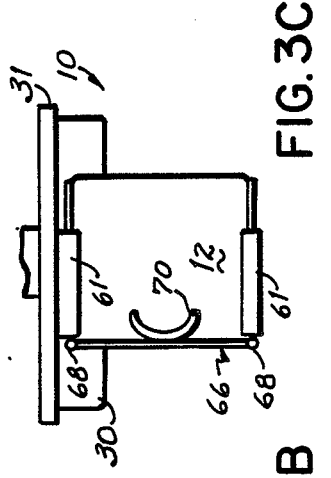
FIG. 2C
FIG. 2B
FIG. 2A
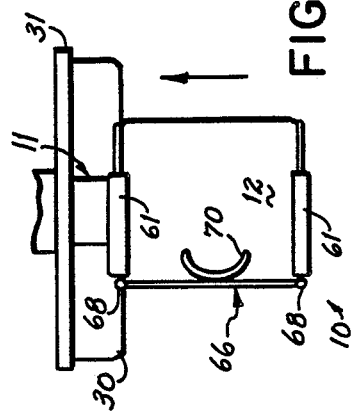
FIG. 3C
FIG. 3B
FIG. 3A
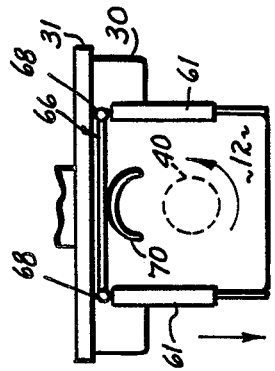

CHAIR FOR X-RAY TABLE

BACKGROUND OF THE INVENTION

This invention relates to a patient chair for facilitating a fluoroscopic examination. Certain patients having muscular disability are unable to swallow properly. Therapy, if properly directed, can improve the patient's ability to swallow. To prescribe proper treatment, the patient's attempts to swallow must be observed so that a precise determination of the muscular involvement and resulting swallowing impairment can be made.

The current practice for observing the patient is to place the patient in front of an X-ray machine with the X-ray table in a substantially vertical orientation. The patient is given liquids of varying consistencies and the patient's attempts to swallow are viewed fluoroscopically. It is these observations that lead to the treatment approach in the first instance with subsequent examinations being made to determine whether the treatments are leading to any improvement in the patient's ability to swallow.

The patient must sit up or stand up. Many patients are so muscularly impaired that they cannot sit up. In these instances, the current practice is to place the X-ray table in a vertical attitude and to raise the foot plate to a position for sitting. The patient is seated on the foot plate with as many as three attendants holding the patient in position for a front view of the swallowing process and thereafter shifting the patient for side views of the process.

BRIEF SUMMARY OF THE INVENTION

An objective of the present invention has been to provide a mechanism for holding a patient on a vertically-oriented X-ray table with the capability of shifting the patient between front and side views.

The foregoing objective of the present invention is attained by providing a base that can be mounted on and fixed to the foot plate of the X-ray table. A seat is mounted to the base by a unit that has a rotatable swivel, fore and aft, and lateral slides. The seat has removable arm, back and headrests for holding a patient in position during the examination.

The mechanism as described permits the following operations for the handling of the patient:

With the X-ray table in the vertical attitude, the chair is secured to the foot plate. The table is then changed to the horizontal attitude taking the chair with it. The patient is then slid from the gurney onto the X-ray table and positioned for seating on the chair. The X-ray table, with patient and chair, is then pivoted to a vertical or substantially vertical attitude. In this attitude, with the fluoroscope operating, a liquid of a preselected consistency is given to the patient. The swallowing is observed and video-recorded.

The slides and swivels are then released and the chair with the patient in it is pulled away from the X-ray table while the base remains fixed to the foot plate. The patient is rotated through 90° and returned to a position against the X-ray table. The swallowing treatment is then repeated. If desired, the patient can be shifted through 180° so that his or her other side is viewed.

BRIEF DESCRIPTION OF THE DRAWINGS

The several features and objectives of the invention will become more readily apparent from the following detailed description taken in conjunction with the drawings in which:

FIGS. 2A, 2B and 2C illustrate preliminary steps in seating the patient on the chair and mounting the chair on the table; and FIGS. 3A, 3B and 3C are diagrammatic top views illustrating the manipulation of the chair.

DETAILED DESCRIPTION OF THE INVENTION

Figure 1:
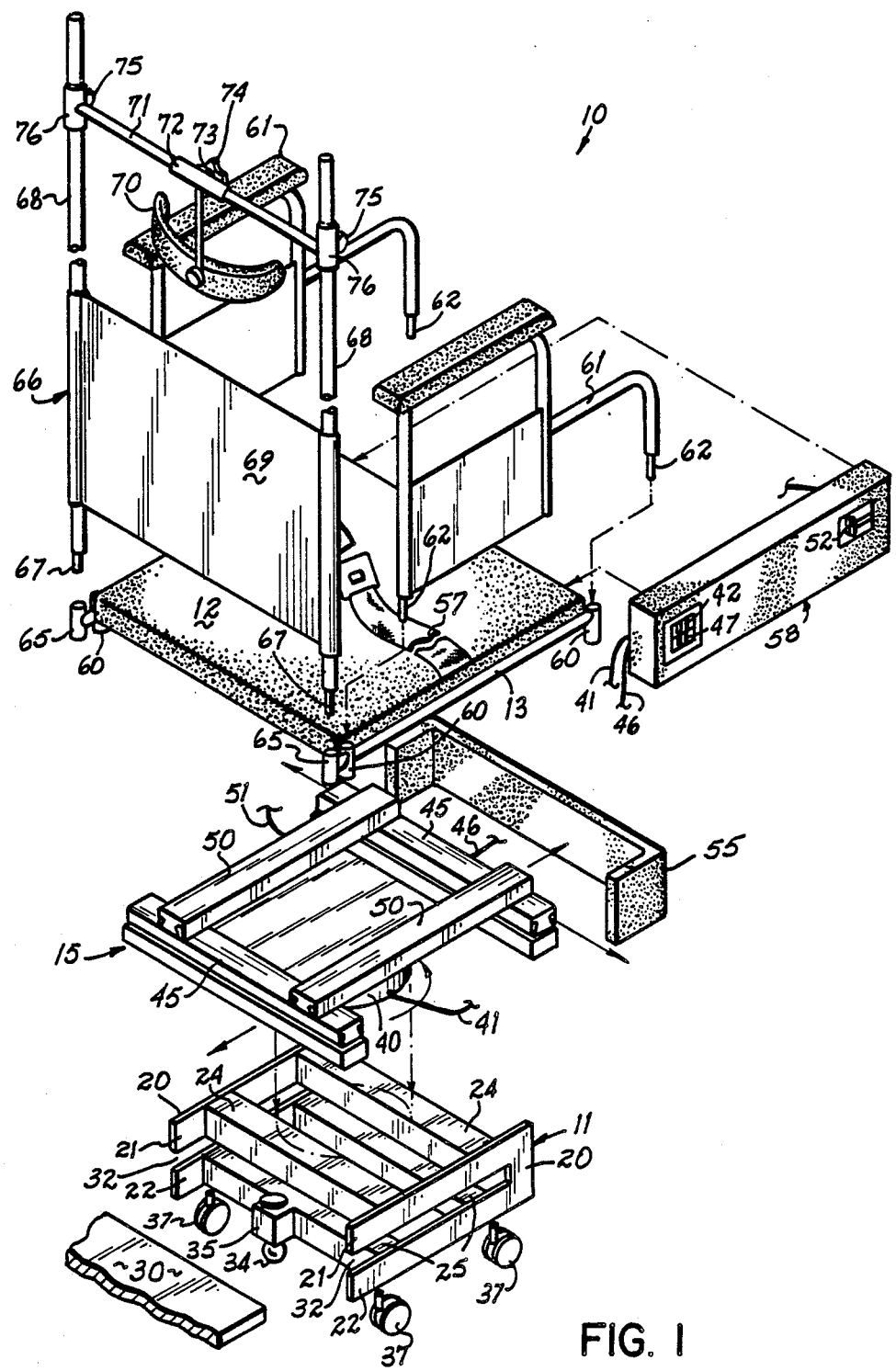
FIG. 1 is a disassembled perspective view of a chair in accordance with the present invention.

The chair of the present invention is shown in 10 in FIG. 1. It has a base 11, a seat 12 secured to a chassis 13 and a swivel and slide unit 15 that secures the seat and chassis to the base. The swivel and slide unit is commercially available and is of the type found supporting captain's chairs in commercial automotive vans wherein the chair can swivel, move fore and aft and side-to-side. Its details are not otherwise shown.

The base has two C-shaped plates 20 presenting upper horizontal legs 21 and lower horizontal legs 22. The plates 20 are joined by upper crossbars 24 and lower crossbars 25, thereby making a rugged base suitable for supporting a patient and for mounting on a foot plate 30 of an X-ray table 31 (FIGS. 2B and 2C). The base 11 is mounted on the foot plate by sliding the foot plate into a slot 32 created between the upper and lower legs 21, 22 of the plates 20. A bolt 34 is threaded in a boss 35 fixed to the bar 25 to fix the base to the foot plate. When the foot plate is in place, the bolt is rotated and bears against the lower surface of the foot plate. A more rapidly manipulated toggle latch is a feasible substitute for the bolt 34 for fixing the base to the foot plate.

Casters 37 are mounted on the lower bars 25 to permit the seat to be conveniently rolled from place to place.

The swivel and slide unit has a swivel 40 secured to the upper bars 24 of the base. The swivel has a flexible cable release 41 that is connected to a release button 42 on the front of the seat.

Above the swivel is a pair of lateral slides 45 that will permit the chair to be slid from side-to-side with respect to the base. A flexible cable 46 is connected to a button 47 on the front of the seat to operate the lateral slide release.

A pair of fore and aft slides 50 are mounted on the lateral slides 45. A flexible cable 51 is connected to a release button 52 on the front of the seat to release the fore and aft slide. An upholstered wrap-around 55 is mounted across the swivel and slide unit to conceal the mechanism.

The seat chassis 13 is fixed to the upper part of the upper slides 50. It carries a seat belt 57 by which the patient is strapped to the seat 12. An upholstered front plate 58 is mounted across the seat chassis and has a lower edge abutting the upper edge of the wrap-around 55 to further conceal the operating mechanism. The operating release buttons 42, 47 and 52 are mounted on front plate 58.

The chassis 13 has, on each side, a pair of sockets 60 to receive removable side arms 61, each side arm having a pair of lower spigots 62 that are slidably-received in the sockets 60. At the rear of the chassis is another pair of sockets 65 which slidably receive a removable backrest 66. The backrest has a pair of lower spigots 67 that are slidably-received in the sockets 65. The spigots 67 are secured to vertical posts 68 to which a back-supporting web 69 is attached. A universally adjustable headrest 70 is secured to a crossbar 71 mounted between the posts 68. An adjustable sleeve 72 and set screw 73 operated by handle 74 are mounted on the bar, thereby permitting manipulation of the headrest. Set screws 75 are mounted on the fittings 76 that mount the crossbar 71 to the posts 68 to permit the vertical adjustment of the crossbar 71.

A typical sequence of steps for the handling of a patient is illustrated in FIGS. 2A through 3C.

As shown in FIG. 2A, the chair is mounted on the X-ray table 31 and is fixed there by the bolt 34. A side arm is removed and the patient, in a supine position, is slid from a cart onto the chair as shown in FIG. 2B. The side arm is replaced, the patient is strapped to the chair by seat belt 57, and the headrest, if needed is adjusted with respect to the patient. The X-ray table 31 is then swung in the direction of the arc 80 until the table, chair and patient are in the attitude of FIG. 2C. There, the liquid to be swallowed is administered and the results are recorded on the video-fluoroscope. That procedure involves the view of the front of the patient swallowing. It is normally desired to view the side of the patient swallowing.

As shown in FIGS. 3A and 3B, the seat and chassis may then be pulled away from the table 31 and the seat rotated through 90° to the position of 3B. Thereafter, the seat is slid on the transverse slide to the position of 3C. There, the swallowing procedure is once again followed. It should be understood that the patient can be viewed from the opposite side by pulling the seat away from the table 31, rotating it through 180° and leading it to a position against the table. In this way, the patient can not only be viewed in the three attitudes discussed, but any angular position in between can be viewed during a swallowing procedure.

It should be further understood that the use of the invention is obviously not restricted to the swallowing procedure, but can be used for other X-ray procedures for patients who are unable to hold themselves in the correct position on a vertically-oriented X-ray table.

From the above disclosure of the general principles of the present invention and the preceding detailed description of a preferred embodiment, those skilled in the art will readily comprehend the various modifications to which the present invention is susceptible.

Therefore, I desire to be limited only by the scope of the following claims and equivalents thereof.

I claim:

1. Apparatus comprising:
a X-ray table having a flat surface,
a foot plate projecting perpendicularly to said table,
a chassis removably clamped to said foot plate,
a chair having a backrest and having a seat parallel to said foot plate,
means mounting said chair on said chassis for fore and aft, lateral and rotational movements to shift a patient, while seated on the chair, between positions in which the patient's back is adjacent said table flat surface and said patient's side in adjacent said table first surface, said shifting including pulling a patient and seat away from said table, rotating the patient and seat 90° and returning said patient and seat to a position adjacent said table.

2. Apparatus as in claim 1 further comprising, armrests,
means for removably mounting said armrests at the sides of said seat,
whereby a patient, in a supine position, can be transferred to and from said seat.

3. Apparatus as in claim 1 further comprising,
a backrest removably mounted on said chair,
and a head stabilizer adjustably mounted on said backrest,
whereby a patient without sufficient muscular control can be held in a steady position, on said chair during the examination procedure.

4. A chair for an X-ray table having a foot plate projecting perpendicularly to said table, said chair comprising,
a seat,
a chassis having a slot to receive said foot plate and means for fixing said chassis to said foot plate,
a swivel mounted on said chassis,
a fore and aft slide and a lateral slide mounted on said swivel,
said seat being mounted on one of said slides,
controls for releasing and fixing said swivel and slides, whereby said seat can be pulled away from said table, rotated 90° and returned to said table to enable viewing a patient in multiple positions with respect to said table.

* * * * *